(12) United States Patent
Heywood

(10) Patent No.: US 8,378,073 B2
(45) Date of Patent: Feb. 19, 2013

(54) PROCESS FOR ATTACHING EFFECTOR MOLECULES TO PROTEINS

(75) Inventor: Sam Philip Heywood, Slough (GB)

(73) Assignee: UCB Pharma S.A. (BE)

( * ) Notice: Subject to any disclaimer, the term of this patent is extended or adjusted under 35 U.S.C. 154(b) by 872 days.

(21) Appl. No.: 11/994,053

(22) PCT Filed: Jun. 29, 2006

(86) PCT No.: PCT/GB2006/002416
§ 371 (c)(1),
(2), (4) Date: Jul. 3, 2008

(87) PCT Pub. No.: WO2007/003898
PCT Pub. Date: Jan. 11, 2007

(65) Prior Publication Data
US 2008/0306246 A1    Dec. 11, 2008

(30) Foreign Application Priority Data

Jul. 6, 2005 (GB) .................................. 0513852.4

(51) Int. Cl.
*C07K 16/00* (2006.01)
(52) U.S. Cl. ....................... 530/345; 530/414; 530/391.1
(58) Field of Classification Search .................. 530/414, 530/345, 391.1
See application file for complete search history.

(56) References Cited

U.S. PATENT DOCUMENTS

| | | | | |
|---|---|---|---|---|
| 4,728,430 A | * | 3/1988 | DiLeo et al. .................. | 210/639 |
| 5,216,183 A | * | 6/1993 | Sugiura et al. ................ | 549/546 |
| 5,225,194 A | * | 7/1993 | Suer ........................... | 424/234.1 |
| 6,146,902 A | * | 11/2000 | McMaster ..................... | 436/177 |
| 6,241,961 B1 | * | 6/2001 | Benes et al. ................. | 424/1.49 |
| 6,406,631 B1 | * | 6/2002 | Collins et al. ................ | 210/646 |
| 6,423,231 B1 | * | 7/2002 | Collins et al. ................ | 210/646 |
| 7,608,694 B2 | * | 10/2009 | Lawson et al. ........... | 530/388.23 |
| 8,067,005 B1 | | 11/2011 | Chapman | |
| 2004/0121415 A1 | * | 6/2004 | King et al. ................... | 435/7.23 |

FOREIGN PATENT DOCUMENTS

| | | |
|---|---|---|
| EP | 0665020 A2 | 8/1995 |
| WO | 98/25971 A1 | 6/1998 |

OTHER PUBLICATIONS

"Series 8000 Stirred Cells and Ultrafiltration Membranes Millipore Data sheet", obtained on Feb. 17, 2011 from http://bit.ly/dODIcd.*
Mather, J. Nucl. Med. 31, 692-697, 1990.*
Ng, Paul, Separation Science 11(5), 499-502, 1976).*
W. F. Blatt, Analytical Biochemistry 26(1), 151-173, 1968.*
Harinarayan, C., Biotechnology and Bioengineering 102(6), 1718-1722, 2009.*
Sesay, M.A., Monoclonal Antibody Conjugation Via Chemical Modification, Biopharm International, 2003, pp. 32-39, vol. 16, No. 12, United States.
Millipore Corporation, 2001, Data Sheet, "Series 8000 Stirred Cells and Ultrafiltration Membranes".
Chapman, A., "PEGylated antibodies and antibody fragments for improved therapy; a review." Advanced Drug and Delivery Reviews, 54 (2002) 531-545.

* cited by examiner

*Primary Examiner* — David Lukton
(74) *Attorney, Agent, or Firm* — McDonnell Boehnen Hulbert & Berghoff

(57) ABSTRACT

The present invention provides a process for attaching one or more effector molecules to one or more cysteines in a protein comprising: a) activating one or more cysteines in the protein by diafiltering the protein against a monothiol reducing agent or a multi-thiol reducing agent which is incapable of forming intramolecular disulphide bonds and b) reacting the treated protein with an effector molecule.

21 Claims, 5 Drawing Sheets

PROCESS FOR ATTACHING EFFECTOR MOLECULES TO PROTEINS

Figure 1:
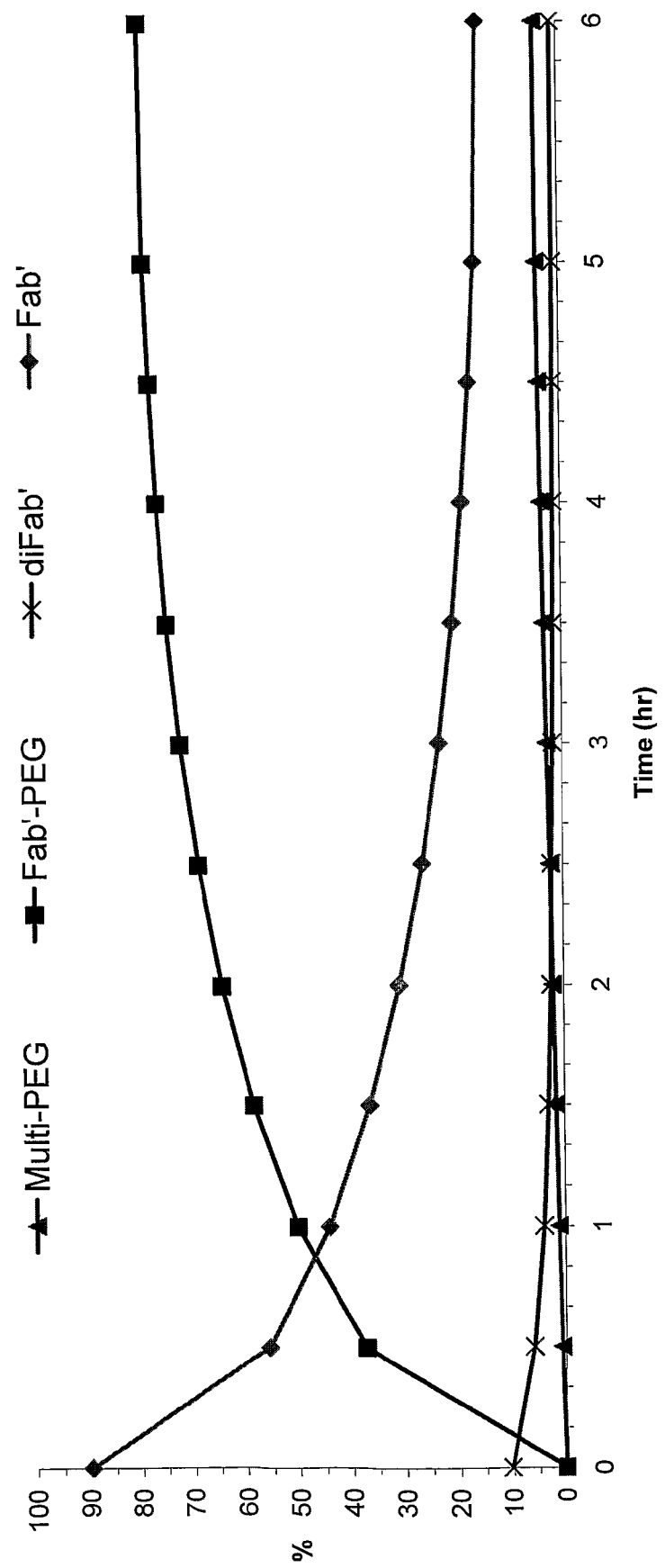

This is a National Stage of International Application No. PCT/GB2006/002416, filed Jun. 29, 2006 which claims foreign priority to U.K. application 0513852.4, filed Jul. 6, 2005.

The present invention relates to processes for attaching effector molecules to proteins and more specifically provides an improved process for the site-specific attachment of one or more effector molecules to one or more cysteines in a protein.

Proteins with effector molecules attached are used for a number of different purposes including both diagnostic and therapeutic uses. The high specificity and affinity of antibody variable regions for example, make them ideal diagnostic and therapeutic agents, particularly for modulating protein:protein interactions. The targeting function encoded in Fv, Fab, Fab', F(ab)$_2$ and other antibody fragments can be conjugated to one or more effector molecules such as cytotoxic drugs, toxins or polymer molecules to increase efficacy. For example, since these fragments lack an Fc region they have a short circulating half-life in animals but this can be improved by conjugation to certain types of polymer such as polyethylene glycol (PEG). Increasing the size of the conjugated PEG has been shown to increase the circulating half-life from minutes to many hours and modification of a Fab' with PEG ranging from 5 kDa to 100 kDa has been demonstrated (Chapman et al., 1999, Nature Biotechnology, 17, 780-783; Leong et al., 2001, Cytokine, 16, 106-119; Chapman, 2002, Advanced Drug Delivery Reviews, 54, 531-545). PEGylated antibody fragments such as CDP870 are currently undergoing clinical trials where the effect of the conjugated PEG is to bring the circulating half-life to acceptable levels for therapy.

Effector molecules can be attached to a protein via a reactive group in the protein which either occurs naturally in the protein or is artificially introduced by protein engineering. Such groups include amines (lysine), thiols (cysteine, methionine), phenols (tyrosine), carboxylic acids (aspartic acid, glutamic acid) or other amino acid side chains. The site of attachment of effector molecules can be either random or site specific although site specific attachment is usually preferred.

The thiol residue from the sulfur containing amino acid cysteine is a commonly used reactive group which can be used for selective coupling of effector molecules to proteins. Site-specific attachment of effector molecules to antibodies for example, is most commonly achieved by attachment to cysteine residues since such residues are relatively uncommon in antibody fragments. Antibody hinges are popular regions for site specific attachment since these contain cysteine residues and are remote from other regions of the antibody likely to be involved in antigen binding. Suitable hinges either occur naturally in the fragment or may be created using recombinant DNA techniques (See for example U.S. Pat. No. 5,677,425; WO98/25971; Leong et al., 2001 Cytokine, 16, 106-119; Chapman et al., 1999 Nature Biotechnology, 17, 780-783). Alternatively site specific cysteines may be engineered into the antibody fragment for example to create surface exposed cysteine(s) (U.S. Pat. No. 5,219,996).

Where effector molecules are to be site specifically attached via a cysteine, the target thiol in the protein is often capped by a small fermentation related peptide product such as glutathione or deliberately capped by a chemical additive used during protein (e.g. antibody fragment) extraction and purification such as 5,5'-dithiobis (2-nitrobenzoic acid) (DTNB). These capping agents need to be removed in order to activate the target thiol before an effector molecule can be attached. In many cases it is desirable to selectively activate one or more target cysteines for effector molecule attachment without reducing other cysteines within the protein. For example, antibody Fab' fragments have a native interchain disulphide bond between the heavy and light chain constant regions ($C_H1$ and $C_L$) and so in order to selectively reduce a target cysteine elsewhere in the antibody, eg. the hinge, reduction must be carried out with some care such that the inter $C_L$:$C_H1$ disulphide remains intact and attachment of effector molecules to the interchain cysteines is avoided. Hence 'mild' reducing conditions are conventionally used to remove the thiol capping agent and activate target thiols prior to reaction with an effector molecule. This mild reduction is usually achieved by incubating the antibody fragment with a thiol based reductant such as β-mercaptoethanol (β-ME), β-mercaptoethylamine (β-MA) or dithiothreitol (DTT) (See for example EP0948544). Following reduction and reaction with effector molecules (under these conditions), a large proportion of the antibody fragments do not have any effector molecules attached and these have to be purified away from the antibody fragments that have the correct number of effector molecules attached. This low efficiency of effector molecule attachment can be a disadvantage during the large-scale production of modified therapeutic antibody fragments where it is important that maximum production efficiency is achieved.

The present invention provides an improved process for selectively attaching one or more effector molecules to one or more cysteines in a protein. In the process of the present invention a greater proportion of protein is correctly modified compared to prior art methods, significantly increasing the efficiency of effector molecule attachment.

Accordingly the present invention provides a process for attaching one or more effector molecules to one or more cysteines in a protein comprising:
 a) activating one or more cysteines in a protein by diafiltering the protein against a monothiol reducing agent or a multi-thiol reducing agent which is incapable of forming intramolecular disulphide bonds and
 b) reacting the treated protein with an effector molecule.

The term 'protein' as used herein includes proteins, polypeptides and fragments thereof containing one or more cysteines which may be used for effector molecule attachment. The proteins may be modified, e.g., to produce variants and fragments thereof, as long as where necessary the desired biological property (e.g. the ability to bind to a target site) is retained. The proteins may be modified by using various genetic engineering or protein engineering techniques, for example to introduce cysteines into the protein for use as sites of effector molecule attachment. Hence the cysteines used for effector molecule attachment may occur naturally in the protein and/or may be engineered into the protein by recombinant DNA techniques. Accordingly, the number and location of cysteines available for the attachment of effector molecules can be specifically controlled depending on the intended use of the protein and the number of effector molecules required.

Examples of suitable proteins include but are not limited to enzymes, hormones, antibodies, receptors, growth factors, serum proteins such as albumin, lipoproteins, and fibrinogen, fibrinolytic enzymes such as tissue plasminogen activator (t-PA), streptokinase, and urokinase, biological response modifiers such as the interleukins, interferons and colony-stimulating factors, erythropoietin, and peptide hormones such as lutenizing hormone, growth hormone, gastrin, follicle-stimulating hormone, TSH, ACTH, IGF binding-proteins, soluble receptors such as IL-1R, TNFR, IL-17R and others.

Preferably the protein to which effector molecules are attached in the process of the present invention is an antibody or fragment thereof. The term 'antibody' as used herein refers to whole antibodies and functionally active fragments or derivatives thereof which may be, but are not limited to, polyclonal, monoclonal, humanized or chimeric antibodies, single chain antibodies, Fv, Fab fragments, Fab' and F(ab')$_2$ fragments and epitope-binding fragments of any of the above. Further examples of suitable antibody fragments also include those described in WO2005003169, WO2005003170 and WO2005003171. Preferably the protein for use in the present invention is a Fab' fragment.

Antibodies therefore include immunoglobulin molecules and immunologically active portions of immunoglobulin molecules, i.e. molecules that contain an antigen-binding site that specifically binds an antigen. The immunoglobulin molecules of the invention can be of any class (e.g. IgG, IgE, IgM, IgD or IgA) or subclass of immunoglobulin molecule and may be obtained from any species including for example mouse, rat, shark, rabbit, pig, hamster, camel, llama, goat or human.

Humanized antibodies are antibody molecules having one or more complementarity determining regions (CDRs) from a non-human species and a framework region from a human immunoglobulin molecule (see, for example, U.S. Pat. No. 5,585,089).

Chimeric antibodies are those antibodies encoded by immunoglobulin genes that have been genetically engineered so that the light and heavy chain genes are composed of immunoglobulin gene segments belonging to different species. Preferably the heavy and light chain constant regions are human and the variable regions are derived from another species.

Monoclonal antibodies may be prepared by any method known in the art such as the hybridoma technique (Kohler & Milstein, *Nature*, 1975, 256, 495-497), the trioma technique, the human B-cell hybridoma technique (Kozbor et al., *Immunology Today*, 1983, 4, 72) and the EBV-hybridoma technique (Cole et al., "Monoclonal Antibodies and Cancer Therapy", pp. 77-96, Alan R. Liss, Inc., 1985).

Antibodies may also be obtained by any other suitable method such as those described in Babcook, J. et al., *Proc. Natl. Acad. Sci. USA*, 1996, 93 (15), 7843-7848, WO 92/02551, WO2004/051268 and WO2004/106377.

Antibody fragments may be obtained from any whole antibody, especially a whole monoclonal antibody, using any suitable enzymatic cleavage and/or digestion techniques, for example by treatment with pepsin. Alternatively, or in addition antibody fragments may be prepared by the use of recombinant DNA techniques involving the manipulation and re-expression of DNA encoding antibody variable and/or constant regions. Standard molecular biology techniques may be used to modify, add or delete amino acids or domains as desired. Any alterations to the variable or constant regions are still encompassed by the terms 'variable' and 'constant' regions as used herein.

The methods for creating and manufacturing antibodies and antibody fragments are well known in the art (see for example, Boss et al., U.S. Pat. No. 4,816,397; Cabilly et al., U.S. Pat. No. 6,331,415; Shrader et al., WO 92/02551; Ward et al., 1989, Nature, 341, 544; Orlandi et al., 1989, Proc. Natl. Acad. Sci. USA, 86, 3833; Riechmann et al., 1988, Nature, 322, 323; Bird et al, 1988, Science, 242, 423; Queen et al., U.S. Pat. No. 5,585,089; Adair, WO91/09967; Mountain and Adair, 1992, Biotechnol. Genet. Eng. Rev, 10, 1-142; Verma et al., 1998, Journal of Immunological Methods, 216, 165-181).

Antibodies and antibody fragments for use in the present invention may possess a native or a modified hinge region comprising one or more cysteines which may be used as sites for effector molecule attachment. The native hinge region is the hinge region normally associated with the $C_H1$ domain of the antibody molecule. A modified hinge region is any hinge that differs in length and/or composition from the native hinge region. Such hinges can include hinge regions from other species, such as human, mouse, rat, rabbit, shark, pig, hamster, camel, llama or goat hinge regions. Other modified hinge regions may comprise a complete hinge region derived from an antibody of a different class or subclass from that of the $C_H1$ domain. Thus, for instance, a $C_H1$ domain of class γ1 may be attached to a hinge region of class γ4. Alternatively, the modified hinge region may comprise part of a natural hinge or a repeating unit in which each unit in the repeat is derived from a natural hinge region. In a further alternative, the natural hinge region may be altered by converting one or more cysteine or other residues into neutral residues, such as serine or alanine, or by converting suitably placed residues into cysteine residues. By such means the number of cysteine residues in the hinge region may be increased or decreased. Other modified hinge regions may be entirely synthetic and may be designed to possess desired properties such as length, cysteine composition and flexibility.

A number of modified hinge regions have already been described for example, in U.S. Pat. No. 5,677,425, WO9915549, WO9825971 and WO2005003171 and these are incorporated herein by reference. In one example the protein for use in the present invention is a Fab' fragment with a native or a modified hinge region.

Alternatively, or in addition, site specific cysteines for effector molecule attachment may be engineered into antibodies or fragments thereof, for example to create surface exposed cysteine(s) (See for example U.S. Pat. No. 5,219,996 and WO2006034488). Thus by using suitable engineering techniques the number of cysteines in an antibody or fragment thereof may be modified in order to provide a specific number of sites for effector molecule attachment.

Hence in one embodiment of the present invention the protein is an antibody Fab' fragment and each cysteine to which an effector molecule is attached is in the hinge. In another embodiment the protein is an antibody Fab' or Fab fragment and at least one cysteine to which an effector molecule is attached is an engineered cysteine, preferably a surface exposed cysteine. In one embodiment two or more effector molecules are attached to an antibody Fab' fragment and at least one of said molecules is attached to a cysteine in the hinge.

Where the protein of the present invention is an antibody or fragment thereof the antibody will in general be capable of selectively binding to an antigen. The antigen may be any cell-associated antigen, for example a cell surface antigen on cells such as bacterial cells, yeast cells, T-cells, endothelial cells or tumour cells, or it may be a soluble antigen. Antigens may also be any medically relevant antigen such as those antigens upregulated during disease or infection, for example receptors and/or their corresponding ligands. Particular examples of cell surface antigens include adhesion molecules, for example integrins such as β1 integrins e.g. VLA-4, E-selectin, P selectin or L-selectin, CD2, CD3, CD4, CD5, CD7, CD8, CD11a, CD11b, CD18, CD19, CD20, CD23, CD25, CD33, CD38, CD40, CD45, CDW52, CD69, carcinoembryonic antigen (CEA), human milk fat globulin (HMFG1 and 2), MHC Class I and MHC Class II antigens, and VEGF, and where appropriate, receptors thereof. Soluble antigens include interleukins such as IL-1, IL-2, IL-3, IL-4, IL-5, IL-6, IL-8, IL-12, IL-16 or IL-17, viral antigens for example respiratory syncytial virus or cytomegalovirus antigens, immunoglobulins, such as IgE, interferons such as interferon α, interferon β or interferon γ, tumour necrosis factor-α, tumor necrosis factor-β, colony stimulating factors such as G-CSF or GM-CSF, and platelet derived growth factors such as PDGF-α, and PDGF-β and where appropriate receptors thereof.

In the process of the present invention at least one effector molecule is covalently linked through a thiol group of a cysteine residue located in the protein. The covalent linkage will generally be a disulphide bond, a thio-ether bond or, in particular, a sulphur-carbon bond. Appropriately activated effector molecules, for example thiol selective derivatives such as maleimide, pyridyldithio, vinylsulfone, iodacetyl, bromoacetyl and cysteine derivatives may be used.

The term 'effector molecule' as used herein includes, for example, antineoplastic agents, drugs, toxins (such as enzymatically active toxins of bacterial or plant origin and fragments thereof e.g. ricin and fragments thereof) biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy. It will be appreciated that an effector molecule may comprise a single effector molecule or two or more such molecules so linked as to form a single moiety that can be attached to a protein using the process of the present invention.

Particular antineoplastic agents include cytotoxic and cytostatic agents for example alkylating agents, such as nitrogen mustards (e.g. chlorambucil, melphalan, mechlorethamine, cyclosphophamide, or uracil mustard) and derivatives thereof, triethylenephosphoramide, triethylenethiophosphor-amide, busulphan, or cisplatin; antimetabolites, such as methotrexate, fluorouracil, floxuridine, cytarabine, mercaptopurine, thioguanine, fluoroacetic acid, or fluorocitric acid, antibiotics, such as bleomycins (e.g. bleomycin sulphate), doxorubicin, daunorubicin, mitomycins (e.g. mitomycin C), actionmycins (e.g. dactinomycin) plicamyin, calicheamicin and derivatives thereof, or esperamicin and derivatives thereof; mitotic inhibitors, such as etoposide, vincristine or vinblastine and derivatives thereof; alkaloids such as ellipticine; polyols such as taxicin-I or taxicin-II; hormones, such as androgens (e.g. dromostanolone or testolactone), progestins (e.g. megestrol acetate or medroxyprogesterone acetate), estrogens (e.g. dimethylstilbestrol diphosphate, polyestradiol phosphate or estramustine phosphate) or antiestrogens (e.g. tamoxifen); anthraquinones, such as mitoxantrone, ureas, such as hydroxyurea; hydrazines, such as procarbazine; or imidazoles, such as dacarbazine.

Chelated metals include chelates of di- or tripositive metals having a coordination number from 2 to 8 inclusive. Particular examples of such metals include technetium (Tc), rhenium (Re), cobalt (Co), copper (Cu), gold (Au), silver (Ag), lead (Pb), bismuth (Bi), indium (In), gallium (Ga), yttrium (Y), terbium (Tb), gadolinium (Gd), and scandium (Sc). In general the metal is preferably a radionuclide. Particular radionuclides include $^{99m}$Tc, $^{186}$Re, $^{188}$Re, $^{58}$Co, $^{60}$Co, $^{67}$Cu, $^{195}$Au, $^{199}$Au, $^{110}$Ag, $^{203}$Pb, $^{206}$Bi, $^{207}$Bi, $^{111}$In, $^{67}$Ga, $^{68}$Ga, $^{88}$Y, $^{90}$Y, $^{160}$Tb, $^{153}$Gd and $^{47}$Sc.

The chelated metal may be for example one of the above types of metal chelated with any suitable polyadentate chelating agent, for example acyclic or cyclic polyamines, polyethers, (e.g. crown ethers and derivatives thereof); polyamides; porphyrins; and carbocyclic derivatives.

In general, the type of chelating agent will depend on the metal in use. One particularly useful group of chelating agents in conjugates according to the invention, however, are acyclic and cyclic polyamines, especially polyaminocarboxylic acids, for example diethylenetriaminepentaacetic acid and derivatives thereof, and macrocyclic amines, e.g. cyclic tri-aza and tetra-aza derivatives (for example as described in International Patent Specification No. WO 92/22583); and polyamides, especially desferriox-amine and derivatives thereof.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, albumin, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741, 900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, rhodamine red, rhodamine green, B-phycoerythrin, R-phycoerythrin, allophycosyanin, Texas red, Pacific blue, Marina blue, Oregon green and the Alexa Fluor series 350, 405, 430, 488, 500, 514, 532, 546, 555, 568, 594, 610, 633, 647, 660, 680, 700 and 750; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

Synthetic or naturally occurring polymers for use as effector molecules include, for example optionally substituted straight or branched chain polyalkylene, polyalkenylene, or polyoxyalkylene polymers or branched or unbranched polysaccharides, e.g. a homo- or hetero- polysaccharide such as lactose, amylose, dextran, starch or glycogen.

Particular optional substituents which may be present on the above-mentioned synthetic polymers include one or more hydroxy, methyl or methoxy groups. Particular examples of synthetic polymers include optionally substituted straight or branched chain poly(ethyleneglycol), poly(propyleneglycol), poly(vinylalcohol) or derivatives thereof, especially optionally substituted poly(ethyleneglycol) such as methoxypoly(ethyleneglycol) or derivatives thereof.

"Derivatives" as used herein is intended to include reactive derivatives, for example thiol-selective reactive groups such as an α-halocarboxylic acid or ester, e.g. iodoacetamide, an imide, e.g. maleimide, a vinyl sulphone or disulphide maleimides and the like. The reactive group may be linked directly or through a linker segment to the polymer. It will be appreciated that the residue of such a group will in some instances form part of the product as the linking group between the protein and the polymer.

The size of the polymer, which may be linear or branched may be varied as desired, but will generally be in an average molecular weight range from 500 Da to 100,000 Da, preferably from 5,000 to 40,000 Da and more preferably from 10,000 to 40,000 Da and 20,000 to 40,000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumor, it may be advantageous to use a small molecular weight polymer, for example with a molecular weight of around 5,000 Da. For applications where the product remains in the circulation, it may be advantageous to use a higher molecular weight polymer, for example having a molecular weight in the range from 25,000 Da to 40,000 Da.

Particularly preferred polymers include a polyalkylene polymer, such as a poly(ethyleneglycol) or, especially, a methoxypoly(ethyleneglycol) or a derivative thereof, and especially with a molecular weight in the range from about 10,000 Da to about 40,000 Da.

The polymers of the present invention may be obtained commercially (for example from Nippon Oil and Fats; Nektar Therapeutics) or may be prepared from commercially available starting materials using conventional chemical procedures.

In a preferred aspect of the present invention at least one of the effector molecules attached to the protein is a polymer molecule, preferably PEG or a derivative thereof. As regards attaching poly(ethyleneglycol) (PEG) moieties in general, reference is made to "Poly(ethyleneglycol) Chemistry, Biotechnical and Biomedical Applications", 1992, J. Milton Harris (ed), Plenum Press, New York; "Poly(ethyleneglycol) Chemistry and Biological Applications", 1997, J. Milton Harris and S. Zalipsky (eds), American Chemical Society, Washington DC and "Bioconjugation Protein Coupling Techniques for the Biomedical Sciences", 1998, M. Aslam and A. Dent, Grove Publishers, New York.

In one example of the present invention each effector molecule attached to the protein is PEG, the protein is an antibody fragment and each PEG molecule is covalently linked via a maleimide group to one or more thiol groups in the antibody fragment. In one preferred embodiment the protein is an antibody Fab' fragment and a PEG molecule is linked via a maleimide group to a single cysteine in the hinge. The PEG may be linear or branched. To attach branched PEG molecules, a lysine residue is preferably covalently linked to the maleimide group. To each of the amine groups on the lysine residue is preferably attached a methoxy(poly(ethyleneglycol) polymer. In one example the molecular weight of each polymer is approximately 20,000 Da and the total molecular weight of the entire polymer molecule is therefore approximately 40,000 Da.

Two or more effector molecules can be attached to cysteines in the protein using the process described herein either simultaneously or sequentially by repeating the process. Preferably if two or more effector molecules are attached to the protein they are attached simultaneously.

The process of the present invention also extends to one or more steps before and/or after the process described herein in which further effector molecules are attached to the protein using any suitable method, for example via other available amino acid side chains such as amino and imino groups. Other such effector molecules may be attached to the protein using standard chemical or recombinant DNA procedures in which the protein is linked either directly or via a coupling agent to the effector molecule. Techniques for conjugating such effector molecules to antibodies for example, are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include for example those described in International Patent Specification numbers WO 93/06231, WO92/22583, WO90/09195, WO89/01476, WO9915549 and WO03031581. Alternatively, where the effector molecule is a protein or polypeptide the linkage may be achieved using recombinant DNA procedures, for example as described in European Patent Specification No. 392745.

In the process of the present invention one or more cysteines are activated in step (a) prior to the attachment of effector molecules. The term 'activating' as used herein refers to the process of producing a free thiol in each cysteine to which an effector molecule is attached in step (b). In one example, 'activating' refers to the removal of an adduct bound to the cysteine, such as glutathione. In another example, 'activating' refers to the reduction of a disulphide bond between two cysteines in different polypeptide chains, for example, reduction of the disulphide bond between one or more hinge cysteines of a $F(ab')_2$ to activate the hinge cysteines of the constituent Fab' fragments. In one embodiment a hinge cysteine of a Fab' fragment is activated by removing an adduct bound to the cysteine. In another embodiment a hinge cysteine of a Fab' fragment is activated by reducing the disulphide bond between two such hinge cysteines in a $F(ab')_2$.

Preferably each cysteine that is activated in step (a) of the process is not in disulphide linkage with another cysteine within the same polypeptide. For example, where the protein is an antibody or fragment thereof, a cysteine activated in step (a) is preferably not the interchain cysteine of the heavy chain, $C_H1$, or the interchain cysteine of the light chain, $C_L$, or an intrachain cysteine of the heavy or light chain. Hence the present invention provides a process whereby effector molecules can be efficiently and selectively attached to specific cysteine residues and other desirable disulphide linkages within the protein can be retained.

In one embodiment of the present invention where the protein is an antibody Fab' fragment the product of the process is an antibody Fab' fragment in which an effector molecule is attached to a single cysteine in the hinge and the interchain disulphide between the heavy and light chain ($C_H1$ and $C_L$) is retained.

In another embodiment two or more proteins may be linked by one or more effector molecules using the process of the present invention. The proteins which may be the same or different can be linked via one or more effector molecules, where appropriate using suitable linkers. In one example, divalent antibodies may be linked by an interchain bridge containing a covalently linked effector molecule. In one such example two Fab' fragments are linked using the process of the present invention to a PEG molecule by appropriate linkers to produce a multi-valent antibody. In one such example, two Fab' fragments are cross-linked with a PEGylated dimaleimide bridge to produce a DFM-PEG as described in WO99/64460.

Cysteines are selectively activated in step (a) of the process of the present invention by diafiltering the protein against a monothiol reducing agent or a multi-thiol reducing agent which is incapable of forming intramolecular disulphide bonds. Diafiltration is a well-known technique in the art and is commonly used for changing the buffer in protein samples. Diafiltration cells are commercially available, for example, the Amicon stirred cell and the Pall Centramate system. A protein sample, typically in a buffer, is diafiltered through a membrane which retains the protein and allows buffer exchange. Over time the original buffer containing the protein is replaced with a new buffer. In the present invention the term 'diafiltered against a monothiol reducing agent or a multithiol reducing agent which is incapable of forming intramolecular disulphide bonds' refers to the diafiltration of a protein against a solvent, suitably a buffer, containing a suitable reducing agent.

Step (a) of the process is generally performed in an aqueous buffer solution examples of which include but are not limited to phosphate or citrate buffer. The protein may be in the same buffer as the diafiltration buffer or they may be different. Preferably the pH of the buffer is in the range of between 2.0 and 10.0, more preferably between 4.0 and 7.0. In one preferred embodiment the buffer pH is between 6.0 and 7.0. The buffer may optionally contain a chelating agent such as EDTA, EGTA, CDTA or DTPA. Preferably the buffer contains EDTA at between 1 and 5 mM, preferably 2 mM. Alternatively or in addition the buffer may be a chelating buffer such as citric acid, oxalic acid, folic acid, bicine, tricine, tris or ADA.

Reducing agents suitable for use in the present invention are monothiol reducing agents and multi-thiol reducing agents which are incapable of forming intramolecular disulphide bonds.

Monothiol reducing agents for use in the present invention are widely known in the art examples of which include, but are not limited to, β-mercaptoethylamine, β-mercaptoethanol, cysteine and glutathione. Preferably the monothiol reducing agent for use in the present invention is β-mercaptoethylamine.

Other suitable reducing agents include multi-thiol reducing agents which are incapable of forming intramolecular disulphide bonds. The term 'multi-thiol reducing agents which are incapable of forming intramolecular disulphide bonds' as used herein refers to reducing agents containing two or more thiol groups which are incapable of forming intramolecular disulphide bonds between the thiol groups. Examples of such reducing agents are shown below:

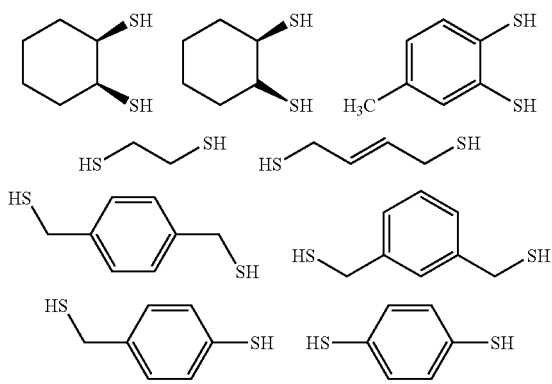

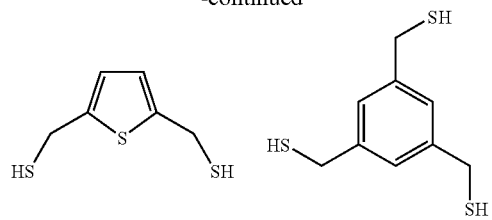

Unsuitable reducing agents for use in the present invention are multi-thiol reducing agents which are capable of forming intramolecular disulphide bonds, for example, dithiothreitol which can form an intramolecular disulphide bond between its two thiol groups.

It will be clear to a person skilled in the art that suitable reducing agents may be identified by determining the number of free thiols produced after the protein is treated with the reducing agent in step (a) or by determining the number of effector molecules attached in step (b) for example by size exclusion chromatography. Methods for determining the number of free thiols are well known in the art, see for example Lyons et al., 1990, Protein Engineering, 3, 703.

Suitable concentrations of reducing agent may also be determined empirically by a person skilled in the art. Preferably the reducing agent is used at a concentration of between 0.3 and 5 mM, more preferably between 0.3 and 4 mM, even more preferably between 0.3 and 3 mM, still more preferably between 0.3 and 2 mM. Preferred concentrations are 1, 1.5, 2, 2.5, 3, 3.5, 4, 4.5, or 5 mM. Preferably the concentration of reducing agent is low in order to achieve selective activation of target cysteines. In one embodiment therefore the concentration of reducing agent does not exceed 5 mM. In one embodiment the concentration of reducing agent does not exceed 4 mM. In one embodiment the concentration of reducing agent does not exceed 3 mM. In one embodiment the concentration of reducing agent does not exceed 2 mM. In one embodiment the concentration of reducing agent does not exceed 1 mM.

In one embodiment of the present invention, prior to the start of diafiltration in step (a) there is no reducing agent present in the protein sample and the protein is brought into contact with the reducing agent by diafiltration. Hence in one embodiment the reducing agent is only incorporated into the diafiltration buffer and there is no reducing agent present in the protein sample prior to step (a) of the process.

In another embodiment reducing agent is also added to the protein prior to diafiltration in step (a). Preferably the reducing agent is added to the protein immediately prior to commencing diafiltration. The reducing agent added to the protein can be the same as the reducing agent in the diafiltration buffer or it may be different. In either case each reductant used is preferably a monothiol reducing agent or a multi-thiol reducing agent which is incapable of forming intramolecular disulphide bonds. Accordingly, in one embodiment the reducing agent added to the protein sample is different to the reducing agent in the diafiltration buffer. Preferably the reducing agent added to the protein is the same as the reducing agent in the diafiltration buffer i.e. a monothiol reducing agent or a multi-thiol reducing agent which is incapable of forming intramolecular disulphide bonds. Preferably the reducing agent in the protein sample and in the diafiltration buffer is β-mercaptoethylamine. Preferably the starting concentration of reducing agent in the protein sample prior to diafiltration is between 0.5 and 1.5 times the concentration of reducing agent in the diafiltration buffer, more preferably between 0.75 and 1.25, even more preferably between 0.9 and 1.1. In one embodiment the concentration of reducing agent in the protein sample at the start of diafiltration is approximately the same as the concentration of reducing agent in the diafiltration buffer, preferably it is the same.

It will be appreciated that the activation of cysteines in a protein in step (a) of the process of the present invention can be optimised by a person skilled in the art by varying the reductant used, the concentration of the reductant, the concentration of the protein, the pH of the reaction, the temperature, the duration of the diafiltration and the flux rate.

Suitable diafiltration flux rates may therefore be determined empirically by a person skilled in the art. Suitable flux rates include between 1 and 15 diavolumes/h. Lower flux rates may also be used, for example between 0.2 and 0.9 diavolumes/h. In one embodiment the flux rate is 0.5 diavolumes/h.

Diafiltration may be conducted at any suitable temperature, for example between about 5° C. and about 70° C., for example at room temperature.

Step (a) of the method is conducted for a time sufficient to activate each cysteine to which an effector molecule is to be attached in step (b). Suitable durations may be determined empirically by one skilled in the art. Typically the diafiltration takes place over a period of between 1 and 20 hours. In one embodiment the diafiltration takes place over a period of between 1 and 10 hours, typically 4, 5, 6, 7, 8, 9 or 10 hours. In one embodiment the diafiltration takes place over a period of 6.5 hours.

A suitable concentration of protein for use in the process of the invention may also be determined empirically by one skilled in the art, depending on the type of protein. For example, where the protein is an antibody Fab' fragment suitable concentrations include between 1 and 200 mg/l, preferably between 2 and 30 mg/l, preferably 20 mg/l.

Optionally, following diafiltration against a reducing agent, the level of the reductant may be reduced or the reductant removed between step (a) and (b) of the process using any suitable method known in the art. In one embodiment the concentration of reductant is reduced by diafiltration of the protein against a buffer which does not contain any reducing agent, for example, by continuing the diafiltration of step (a) against this new buffer. In another embodiment the level of reductant is reduced by diafiltration against a buffer containing a lower concentration of reducing agent. In another embodiment, the level of reductant is reduced or the reductant is removed from the protein sample by gel filtration.

In step (b) of the process one or more effector molecules are reacted with the treated protein produced in step (a) of the method in order to attach an effector molecule to the activated cysteine(s).

Step (b) of the process may generally be performed in a solvent, for example an aqueous buffer solution such as phosphate, citrate or acetate. Typically this is the buffer into which the protein sample has been diafiltered or transferred by gel filtration. The reaction may generally be performed at any suitable temperature, for example between about 5° C. and about 70° C., for example at room temperature. The buffer may optionally contain a chelating agent such as EDTA, EGTA, CDTA or DTPA. Preferably the buffer contains EDTA at between 1 and 5 mM, preferably 2 mM. Alternatively or in addition the buffer may be a chelating buffer such as citric acid, oxalic acid, folic acid, bicine, tricine, tris or ADA. The effector molecule will generally be employed in at least equimolar concentration relative to the concentration of the protein i.e. at least 1:1. Typically the effector molecule will be employed in excess concentration relative to the concentration of the protein. Typically the effector molecule is in between 1.1 and 100 fold molar excess, preferably 1.1, 1.5, 2, 3, 5, 10 or 50 fold molar excess. Further examples of suitable effector molecule concentrations include a 1.2, 1.25, 1.3 and 1.4 fold molar excess. Alternatively where 2 or more proteins are attached to one or more effector molecules the effector molecule may not be in excess, for example the ratio of effector molecule to protein may be between 0.1 and 1, preferably 0.5. The duration of the reaction may be determined empirically by a person skilled in the art and is typically between 1 and 20 hours. In one embodiment the reaction takes place over a period of 14-16 hours.

Where necessary, the desired product containing the desired number of effector molecules may be separated from any starting materials or other products generated during the process by conventional means, for example by chromatography techniques such as ion exchange, size exclusion or hydrophobic interaction chromatography. Hence in one embodiment the process of the present invention further comprises step (c) in which the protein with the desired number of effector molecules attached is purified.

EXAMPLES

The present invention will now be described by way of example only, in which reference is made to:

FIG. 1: Effect of reduction time on PEGylation efficiency of a Fab'.

Figure 2:
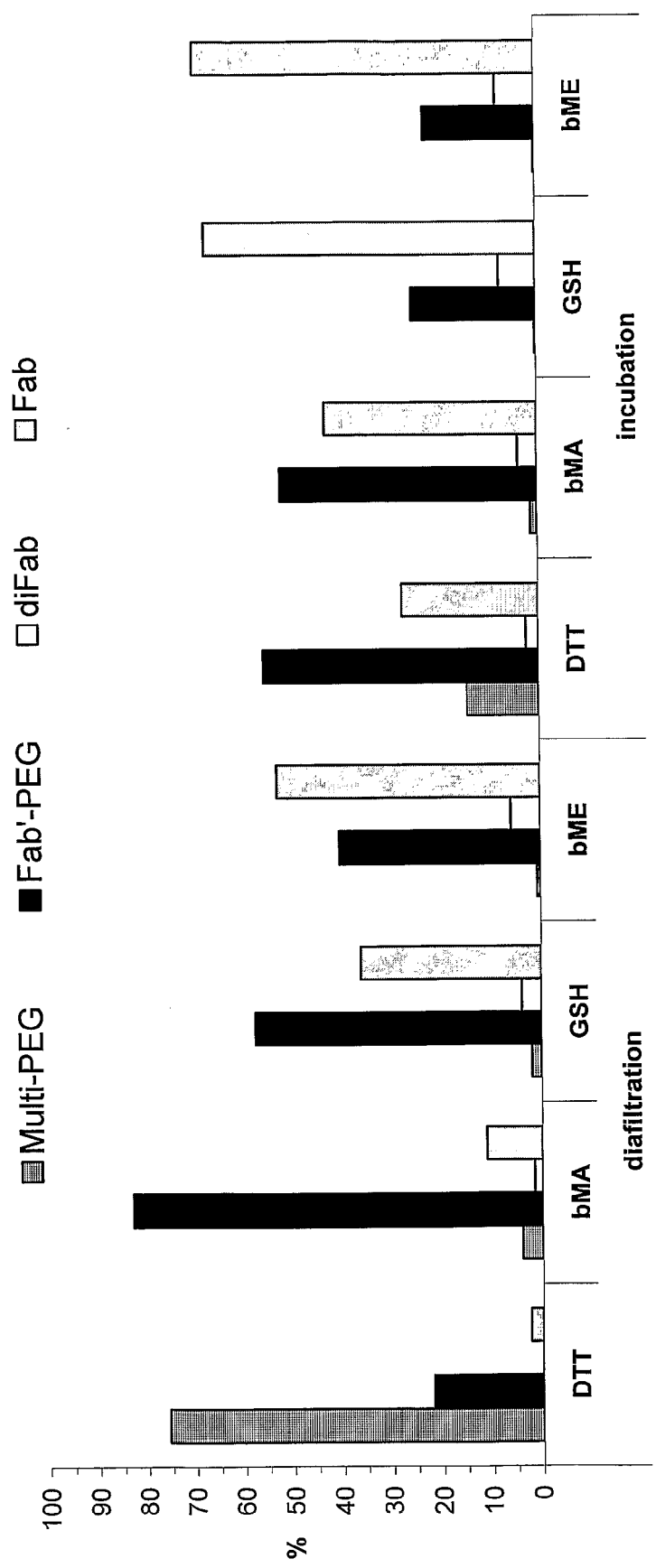

FIG. 2: A comparison of the effect of reducing conditions on PEGylation efficiency.

Figure 3:
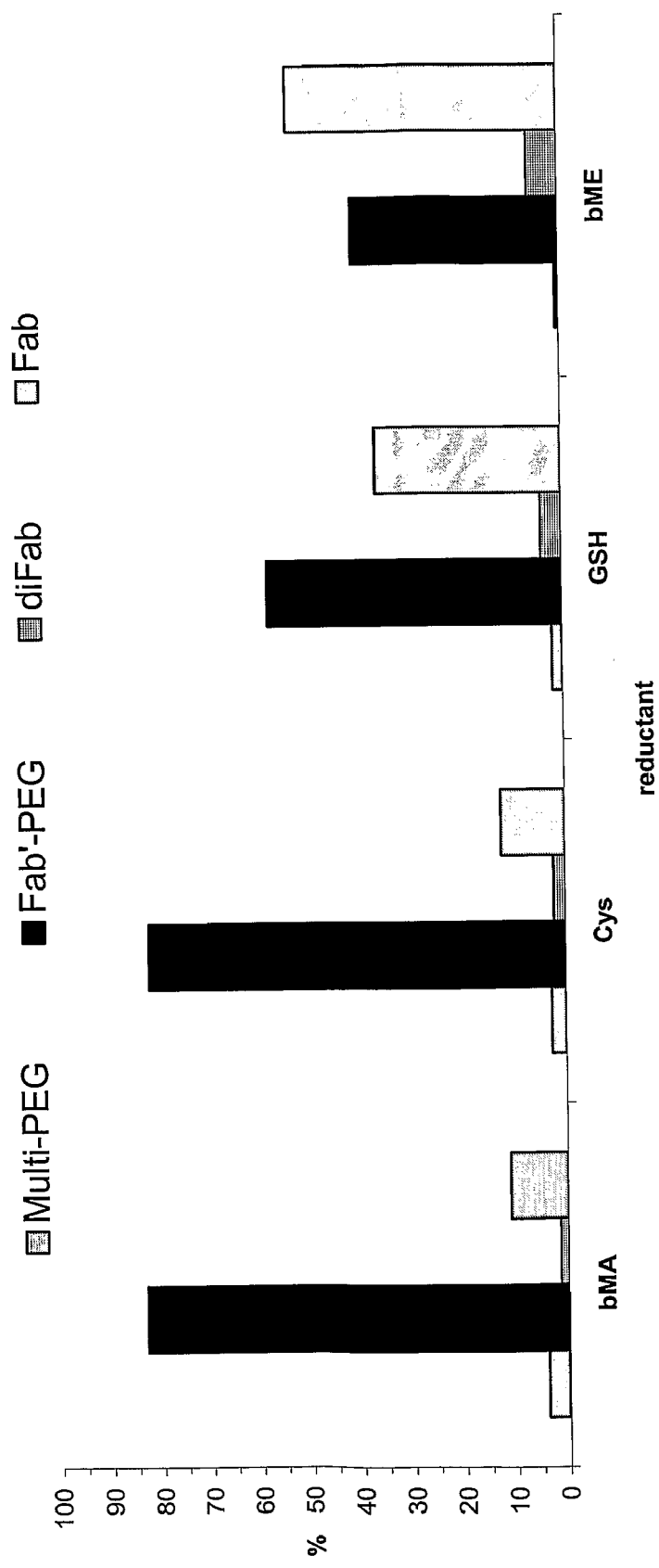

FIG. 3: A comparison of the effect of reductant type on PEGylation efficiency

Figure 4:
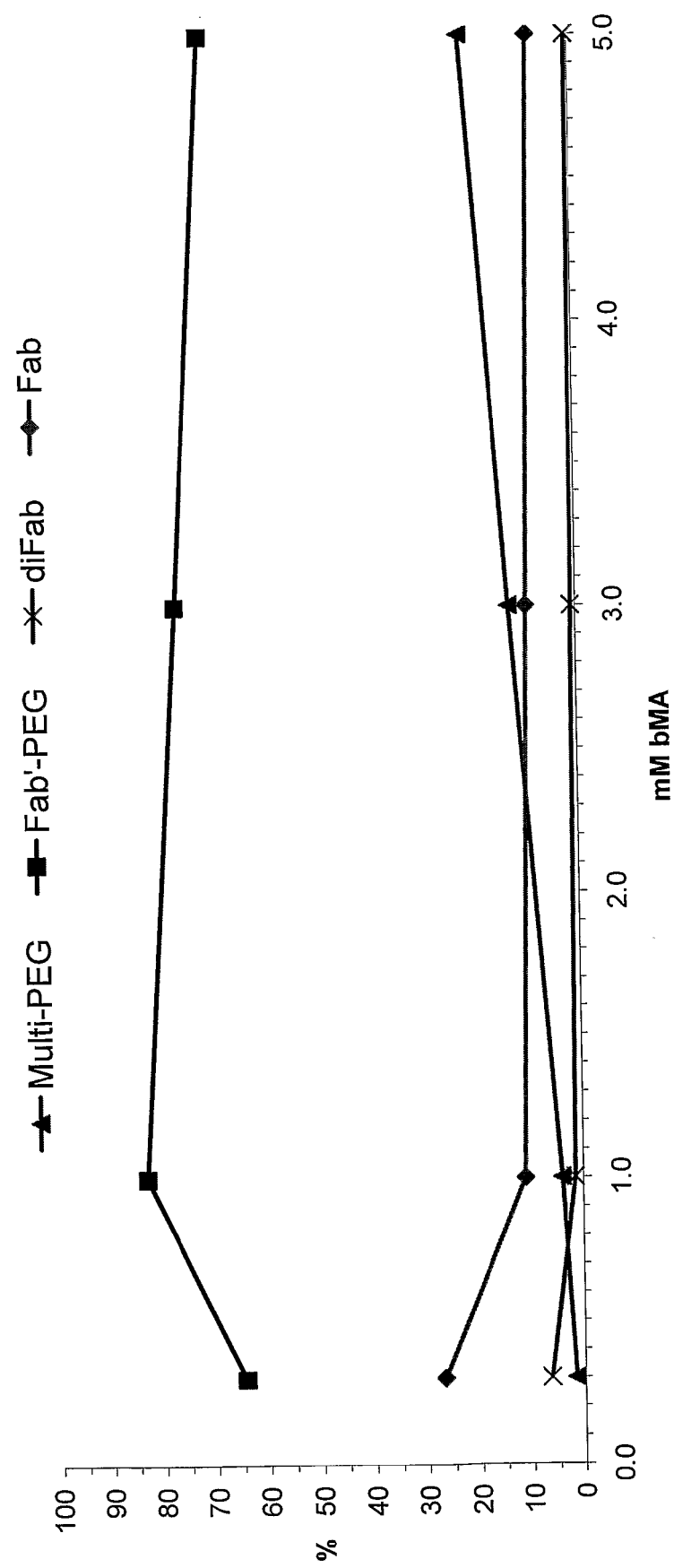

FIG. 4: Effect of reductant concentration on PEGylation efficiency.

Figure 5:
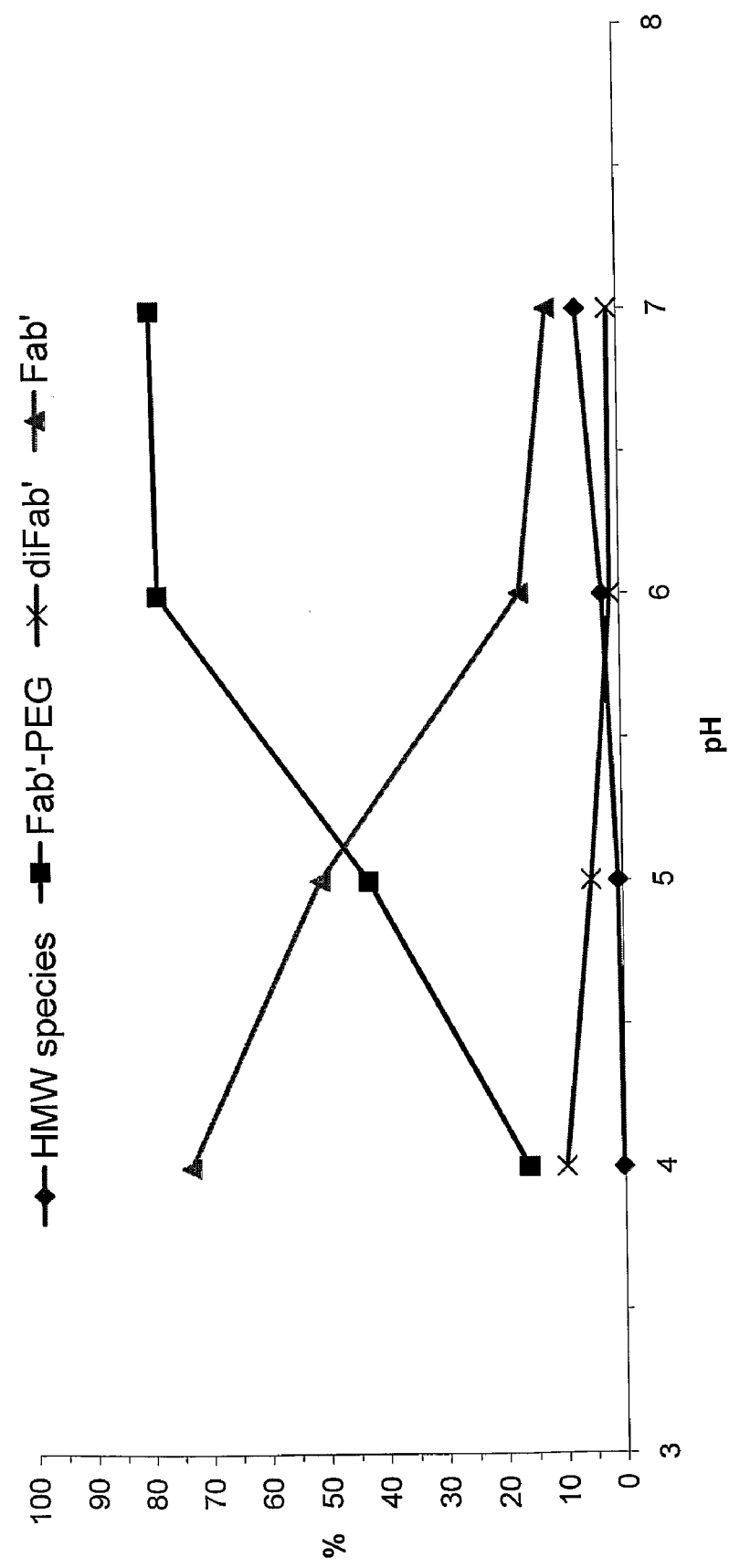

FIG. 5: Effect of pH on PEGylation efficiency.

The term 'Fab'-PEG' in all figures represents a Fab' with one 40,000 PEG attached to the single hinge cysteine.

The term 'Multi-PEG' in all figures represents High Molecular Weight PEGylated material in which greater than 1 PEG molecule is attached to the antibody Fab' fragment.

Example 1

20 ml of Fab' containing a single hinge thiol at 10 mg/ml in 0.1M phosphate, 2 mM EDTA pH6 was reduced by diafiltration in a 8050 Amicon stirred cell with a 10000 MWCO membrane against 2 mM 2-mercaptoethylamine, 0.1M phosphate, 2 mM EDTA pH6. Immediately prior to the start of the diafiltration 2-mercaptoethylamine was added to the Fab' solution to a final concentration of 2 mM.

During diafiltration 1 ml aliquots of the retentate were removed every 30 min and the reductant was removed from the aliquot by stringent gel filtration on a PD 10 column equilibrated with 0.1M phosphate, 2 mM EDTA pH6. The reduced Fab' was PEGylated in the same buffer with ~3 fold molar excess of 40 kPEG-maleimide (Nektar) at ambient temperature for 16 hours. PEGylation of the Fab' (percentage PEGylated) was measured by size exclusion HPLC.

FIG. 1 shows the progression over time of the reaction to an equilibrium of ~80% monoPEGylation of the Fab' after 5 hours of diafiltration.

Example 2

8 ml samples of Fab' containing a single hinge thiol at 10 mg/ml in 0.1M phosphate, 2 mM EDTA pH6 were reduced by diafiltration in 8010 Amicon stirred cells with a 10000

MWCO membranes against 1 mM 2-mercaptoethylamine or 1 mM 2-mercaptoethanol or 1 mM reduced glutathione or 1 mM dithiothreitol all in 0.1M phosphate, 2 mM EDTA pH6 for 16 hours at ambient temperature. The reductants were then removed by continued diafiltration of the Fab's against 0.1M phosphate, 2 mM EDTA pH6 for 4 hours at ambient temperature. The reduced Fab's were PEGylated in the same buffer with a 5 fold molar excess of 40 kPEG-maleimide (Nektar) at ambient temperature for 16 hours.

In parallel 0.5 ml samples of Fab' containing a single hinge thiol at 10 mg/ml in 0.1M phosphate, 2 mM EDTA pH6 were reduced by incubation with 5 mM 2-mercaptoethylamine or 5 mM 2-mercaptoethanol or 5 mM reduced glutathione or 5 mM dithiothreitol for 30 minutes at ambient temperature. The reductants were removed by stringent gel filtration on a PD10 column equilibrated with 0.1M phosphate, 2 mM EDTA pH6. The reduced Fab's were PEGylated with a 5 fold molar excess of 40 k PEG-maleimide (Nektar) at ambient temperature for 16 hours.

PEGylation of the Fab' was measured by size exclusion HPLC and reducing and non-reducing SDS-PAGE. SDS-PAGE analysis demonstrated that the interchain disulphide was retained in the Fab'-PEG (monopegylated).

FIG. 2 shows that diafiltration reduction pushes the equilibrium towards more monoPEGylation of the Fab' compared to incubation which results in a large proportion of the Fab' remaining unPEGylated. Diafiltration using 2-mercaptoethylamine increased the percentage of Fab' that was monoPEGylated from 55 to 85%. Similarly diafiltration using glutathione or 2-mercaptoethanol increased the percentage of Fab' that was monoPEGylated from 25% to 58% and from 22% to 42% respectively. FIG. 2 also shows that if the reductant is a di-thiol capable of forming an intramolecular disulphide bond e.g. dithiothreitol it pushes the equilibrium past monoPEGylation to undesirable extensive multiPEGylation onto the interchain cysteines.

Example 3

8 ml samples of Fab' containing a single hinge thiol at 10 mg/ml in 0.1M phosphate, 2 mM EDTA pH6 were reduced by diafiltration in 8010 Amicon stirred cells with a 10000 MWCO membranes against 1 mM 2-mercaptoethylamine or 1 mM 2-mercaptoethanol or 1 mM reduced glutathione or 1 mM L-cysteine all in 0.1M phosphate, 2 mM EDTA pH6 for 16 hours at ambient temperature. The reductants were then removed by continued diafiltration of the Fab's against 0.1M phosphate, 2 mM EDTA pH6 for 4 hours at ambient temperature. The reduced Fab's were PEGylated with a 5 fold molar excess of 40 kPEG-maleimide (Nektar) at ambient temperature for 16 hours.

PEGylation of the Fab' was measured by size exclusion HPLC and reducing and non-reducing SDS-PAGE.

FIG. 3 shows that both β-mercaptoethylamine and cysteine are particularly efficient at reducing the Fab' to give high levels of monoPEGylation.

Example 4

6 ml samples of Fab' containing a single hinge thiol at 10 mg/ml in 0.1M phosphate, 2 mM EDTA pH6 were reduced by diafiltration in 8010 Amicom stirred cells with a 10000 MWCO membranes against 0.3 mM or 1 mM or 3 mM or 5 mM 2-mercaptoethylamine in 0.1M phosphate, 2 mM EDTA pH6 for 16 hours at ambient temperature. The reductant was then removed by continued diafiltration of the Fab's against 0.1M phosphate, 2 mM EDTA pH6 for 4 hours at ambient temperature. The reduced Fab's were PEGylated with a 3 fold molar excess of 40 kPEG-maleimide (Nektar) at ambient temperature for 16 hours.

PEGylation of the Fab' was measured by size exclusion HPLC and reducing and non-reducing SDS-PAGE.

FIG. 4 shows that the efficiency of the reduction is dependent on the concentration of the reductant. 1 mM was found to be optimal for this Fab' under these conditions. It will be appreciated that reduction of any protein can be optimised by varying the reductant used, the concentration of the reductant, the concentration of the protein, the pH of the reaction, the temperature, the amount of the reductant passed through the protein and the flux rate of the reductant passing through the protein.

Example 5

6.5 ml samples of Fab' at 10 mg/ml in 0.1M citrate, 2 mM EDTA pH4, 5, 6 or 7 were reduced by diafiltration in 8010 Amicom stirred cells with a 10000 MWCO membranes against 1 mM 2-mercaptoethylamine in 0.1M citrate, 2 mM EDTA pH4, 5, 6 or 7 for 16 hours at ambient temperature. The reductant was removed by stringent gel filtration on PD10 columns equilibrated with 0.1M citrate, 2 mM EDTA pH4, 5, 6 or 7. The reduced Fab's were PEGylated with a 4 fold molar excess of 40 kPEG-maleimide (Nektar) at ambient temperature for 5 hours.

PEGylation of the Fab' was measured by size exclusion HPLC.

FIG. 5 shows the effect of pH on the amount of Fab'-PEG produced.

Example 6

Antibody Fab' at 20 mg/ml (±2 mg/ml) in 0.1M phosphate, 2 mM EDTA, pH 6.8 was reduced by diafiltration using a 10000 MWCO membrane in a volume of 15-20 litres against 1 mM 2-mercaptoethylamine in 0.1M phosphate, 2 mM EDTA pH 6.8 for 6.5 hours at a flux rate of 1 diafiltration volume/h at ambient temperature. Immediately prior to the start of the diafiltration 2-mercaptoethylamine was added to the Fab' solution to a final concentration of 1 mM. Following diafiltration the reductant was removed by continued diafiltration at 8 diafiltration volumes/h against 20 mM sodium acetate pH 4.5 for between 1 and 1.5 hours.

The reduced Fab' was incubated with a 1.25 molar excess of 40 kPEG-maleimide (Nektar) at ambient temperature for between 16 and 20 hours.

PEGylation of the Fab' was measured by size exclusion HPLC. 85% PEGylation was achieved.

The diafiltration process was confirmed to be effective at large scale, resulting in a high efficiency of PEGylation.

The invention claimed is:

1. A process for attaching one or more effector molecules to one or more cysteines in a protein sample comprising:
    a) activating one or more cysteines in the protein sample by commencing diafiltration of the protein sample against a diafiltration buffer, wherein the diafiltration buffer comprises a monothiol reducing agent or a multi-thiol reducing agent which is incapable of forming intramolecular disulphide bonds thereby forming a treated protein, and
    b) reacting the treated protein with an effector molecule.

2. The process according to claim 1 in which a monothiol reducing agent or a multi-thiol reducing agent which is incapable of forming intramolecular disulphide bonds is present in the protein sample prior to step (a).

3. The process according to claim 2 in which the concentration of reducing agent in the protein sample is between 0.5 and 1.5 times the concentration of reducing agent in the diafiltration buffer.

4. The process according to claim 3 in which prior to step (a) the concentration of reducing agent in the protein sample is the same as the concentration of reducing agent in the diafiltration buffer.

5. The process according to claim 1 in which the concentration of reducing agent is 1 mM.

6. The process according to claim 1 in which the reducing agent is removed from the protein sample between step (a) and step (b).

7. The process according to claim 6 in which the reducing agent is removed by gel filtration.

8. The process according to claim 6 in which the reducing agent is removed by diafiltration.

9. The process according to claim 1 in which the reducing agent is selected from β-mercaptoethylamine, β-mercaptoethanol, glutathione or cysteine.

10. The process according to claim 1 further comprising step (c) in which the protein with the desired number of effector molecules attached is purified.

11. The process according to claim 1 in which the protein is an antibody or fragment thereof.

12. The process of claim 11 in which the protein is an antibody Fab' fragment.

13. The process according to claim 11 in which at least one cysteine to which an effector molecule is attached is present in the antibody hinge.

14. The process according to claim 13 in which each cysteine to which an effector molecule is attached is present in the antibody hinge.

15. The process according to claim 1 in which the effector molecule is PEG.

16. The process according to claim 15 in which the effector molecule is 40,000 PEG-maleimide.

17. The process according to claim 2 in which the reducing agent is removed from the protein sample between step (a) and step (b).

18. The process according to claim 2 in which the reducing agent is selected from β-mercaptoethylamine, β-mercaptoethanol, glutathione or cysteine.

19. The process according to claim 2 further comprising step (c) in which the protein with the desired number of effector molecules attached is purified.

20. The process according to claim 2 in which the protein is an antibody or fragment thereof.

21. A process for attaching one or more effector molecules to one or more cysteines in a protein sample comprising:
  a) activating one or more cysteines in the protein sample, the cysteines that are activated being not in disulphide linkage with another cysteine in the same polypeptide, by diafiltering of the protein sample against a diafiltration buffer, wherein the diafiltration buffer comprises a monothiol reducing agent or a multi-thiol reducing agent which is incapable of forming intramolecular disulphide bonds thereby forming a treated protein, and
  b) reacting the treated protein with an effector molecule.

* * * * *

UNITED STATES PATENT AND TRADEMARK OFFICE
CERTIFICATE OF CORRECTION

| | | |
|---|---|---|
| PATENT NO. | : 8,378,073 B2 | Page 1 of 1 |
| APPLICATION NO. | : 11/994053 | |
| DATED | : February 19, 2013 | |
| INVENTOR(S) | : Heywood | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1259 days.

Signed and Sealed this
Thirtieth Day of December, 2014

Michelle K. Lee
*Deputy Director of the United States Patent and Trademark Office*